US00PP32260P3

(12) United States Plant Patent
Nontaswatsri

(10) Patent No.: US PP32,260 P3
(45) Date of Patent: Sep. 29, 2020

(54) ***CURCUMA* PLANT NAMED 'MAROON HEART'**

(50) Latin Name: ***Curcuma* hybrid**
Varietal Denomination: Maroon Heart

(71) Applicant: Agricultural Research Development Agency, Bangkok (TH)

(72) Inventor: Chalermsri Nontaswatsri, Bangkok (TH)

(73) Assignee: Agricultural Research Development Agency, Bangkok (TH)

( * ) Notice: Subject to any disclaimer, the term of this patent is extended or adjusted under 35 U.S.C. 154(b) by 0 days.

(21) Appl. No.: 16/501,648

(22) Filed: May 16, 2019

(65) Prior Publication Data

US 2019/0357410 P1 Nov. 21, 2019

Related U.S. Application Data

(60) Provisional application No. 62/762,730, filed on May 17, 2018.

(51) Int. Cl.
*A01H 5/02* (2018.01)
*A01H 6/00* (2018.01)

(52) U.S. Cl.
USPC ..... Plt./421
CPC ..... *A01H 6/00* (2018.05); *A01H 5/02* (2013.01)

(58) Field of Classification Search
USPC ..... Plt./421
See application file for complete search history.

*Primary Examiner* — Susan McCormick Ewoldt
(74) *Attorney, Agent, or Firm* — The Webb Law Firm

(57) ABSTRACT

A new and distinct *curcuma* plant having long, deep red colored inflorescences.

1 Drawing Sheet

Botanical classification: *Curcuma* hybrid.
Varietal denomination: 'Maroon Heart'.

BACKGROUND OF THE INVENTION

The present invention comprises a new and distinct variety of *curcuma* plant known by the varietal name 'Maroon Heart'. The new variety was discovered in 2016 in Chiangmai, Thailand as the result of a planned breeding program with the purposes of providing *curcuma* plants with new coloration and characteristics. The new variety is the result of a cross between an unnamed and unpatented *Curcuma alismatifolia* variety (female parent) and an unnamed and unpatented *Curcuma aurantiaca* variety (male parent). The new variety is similar to its female parent in exhibiting flowers with a purple colored lip, but differs from its female parent in having a red inflorescence color versus a pink inflorescence color of its female parent. 'Maroon Heart' has a similar red inflorescence color to its male parent, but exhibits a different lip flower color (dark purple and yellow for 'Maroon Heart' versus yellow for its male parent) and longer inflorescences than its male parent. Tissue culture and bulb asexual reproductions of the new variety first occurred in 2016 in Chiangmai, Thailand. 'Maroon Heart' has been trial and field tested and has been found to retain its distinctive characteristics and remain true to type through successive propagations. The present invention has not been evaluated under all possible environmental conditions. The phenotype may vary with variations in environment without a change in the genotype of the plant.

Its large, long, and deep red inflorescences distinguish 'Maroon Heart' from other *curcuma* varieties known to the breeder. Further, when 'Maroon Heart' is compared to *Curcuma* hybrid 'Apollo' (U.S. Plant patent application Ser. No. 16/501,644), the varieties are similar in inflorescence height and exhibiting a red colored leaf midrib. However, the varieties differ in inflorescence color ('Maroon Heart' has darker red colored inflorescences than 'Apollo').

DESCRIPTION OF THE DRAWING

The accompanying photographic drawing taken at approximately 60 days of age illustrates the new variety, with the colors being as nearly true as is possible with color illustrations of this type.

DESCRIPTION OF THE PLANT

The following detailed description sets forth the characteristics of the new variety at approximately 60 days of age. The data which defines these characteristics was collected under natural light in Chiangmai, Thailand. Plants of the new variety were grown in 20.3 cm pots in a plastic greenhouse in Chiangmai, Thailand and watered 1-2 times a day, if needed. Color references are primarily to the 2016 HTML Color Chart and The 2015 R.H.S. Colour Chart of The Royal Horticultural Society of London, 6th Edition, except where general color terms are used.

PLANT

Time to initiate roots: About 20-30 days at about 30-33° C.
Time to produce a rooted young plant: About 45 days at about 30-33° C.
Root description: Fibrous, with a pale yellow colored (FAFCF5) milk tank.
Number of rhizomes produced per plant: From 1-3.
Rhizome diameter: 3.0 cm.
Growth habit: Annual.

Plant height (soil level to top of inflorescences): 40.0-50.0 cm.
Plant diameter: 30.0-40.0 cm.
Pubescence: None observed.
Disease resistance/susceptibility: None observed.
Pest resistance/susceptibility: None observed.
Temperature tolerance: 20-40° C. or tropical climate conditions.
Drought tolerance: Unknown.
Seed/fruit: None observed to date.
Leaves:
*Arrangement*.—Alternate.
*Average number per plant*.—5.
*Length*.—27.0 cm.
*Width*.—8.0 cm.
*Shape of leaf* (*generally*).—Moderately elliptic.
*Shape of apex*.—Attenuate.
*Shape of base*.—Narrow.
*Margin description*.—Entire.
*Texture*.—Upper surface: Smooth. Lower surface: Pubescence present.
*Aspect*.—Upright.
*Color*.—Young leaves: Upper surface: Green (779146). Lower surface: Green (41542E). Mature leaves: Upper surface: Green (344528). Lower surface: Green (31481E).
*Veins*.—Appearance: Pinnate and penninerved. Color: Upper surface: Green with a red (807976) midrib. Lower surface: Green with a red (807976) midrib.
*Leaf sheaths*.—Length: 12.0 cm. Width: 2.0 cm. Texture: Upper surface: Smooth. Lower surface: Smooth. Color: Upper surface: RHS 142A. Lower surface: RHS 142A. Venation: Pattern: Parallel. Color: RHS 71B.

INFLORESCENCE

Inflorescence arrangement: 1 inflorescence per shoot.
Inflorescence number per plant: From 2-3.
Inflorescence length: 20.0 cm.
Inflorescence diameter: 7.0 cm.
Fragrance: None.
Flower bracts:
*Total number per inflorescence*.—Approximately 20.
*Upper bracts*.—Number: Approximately 10. Length: 5.0 cm. Width: 3.0 cm. Shape: Elliptic. Apex: Acuminate. Base: Shallow U-shaped. Margin: Entire. Texture: Upper surface: Smooth. Lower surface: Smooth. Color: Upper surface: Red (720C1A). Lower surface: Red (720C1A).
*Lower bracts*.—Number: Approximately 10. Length: 3.0 cm. Width: 3.0 cm. Shape: Orbicular. Apex: Obtuse. Base: U-shaped. Margin: Entire. Texture: Upper surface: Smooth. Lower surface: Smooth. Color: Upper surface: Red (5D2F39). Lower surface: Red (5D2F39).

Flowers:
*Number per inflorescence*.—Approximately 50.
*Continuity of flowering*.—1 month.
*Lastingness of an individual flower*.—1-2 days.
*Length*.—3.5-4.0 cm.
*Diameter*.—2.0 cm.
*Appearance*.—Orchidaceous form.
*Upper petals*.—Upper surface color: Pale yellow (C2997F). Lower surface color: Pale yellow (C2997F).
*Lower petals*.—Upper surface color: Pale yellow (C2997F) with purple (934267) on labellum ridge. Lower surface color: Pale yellow (C2997F).
*Flower buds*.—Length: 4.0 cm. Diameter: 0.7 cm. Shape: Round. Texture: Smooth. Color: RHS 63B.
*Sepals*.—Number: 3. Calyx arrangement: In overlapping circles. Length: 1.5 cm. Width: 1.0 cm. Overall shape: Elliptic. Apex: Elliptic. Base: Connected in a cone shape. Texture: Smooth (both surfaces). Color: Upper surface: RHS 63B. Lower surface: RHS 65C.
Peduncles:
*Length*.—20.0 cm.
*Diameter*.—1.0 cm.
*Texture*.—Smooth.
*Angle*.—Upright.
*Color*.—Green (777F3F).

REPRODUCTIVE ORGANS

Stamens:
*Number*.—1.
Filament:
*Length*.—2.0 cm.
*Diameter*.—1.0 mm.
*Color*.—Pale cream (C6AE98).
Anthers:
*Shape*.—2-lobed.
*Length*.—3.0 mm.
*Color*.—Cream (B88967).
Pollen: None observed.
Pistils:
*Number*.—1.
*Length*.—1.0 cm.
Style:
*Length*.—1.0 cm.
*Diameter*.—2.0 mm.
*Color*.—Cream (B88967).
Stigma:
*Length*.—2.0 mm.
*Diameter*.—2.0 mm.
*Color*.—Cream (B88967).

I claim:

1. A new and distinct variety of *curcuma* plant, as is herein illustrated and described.

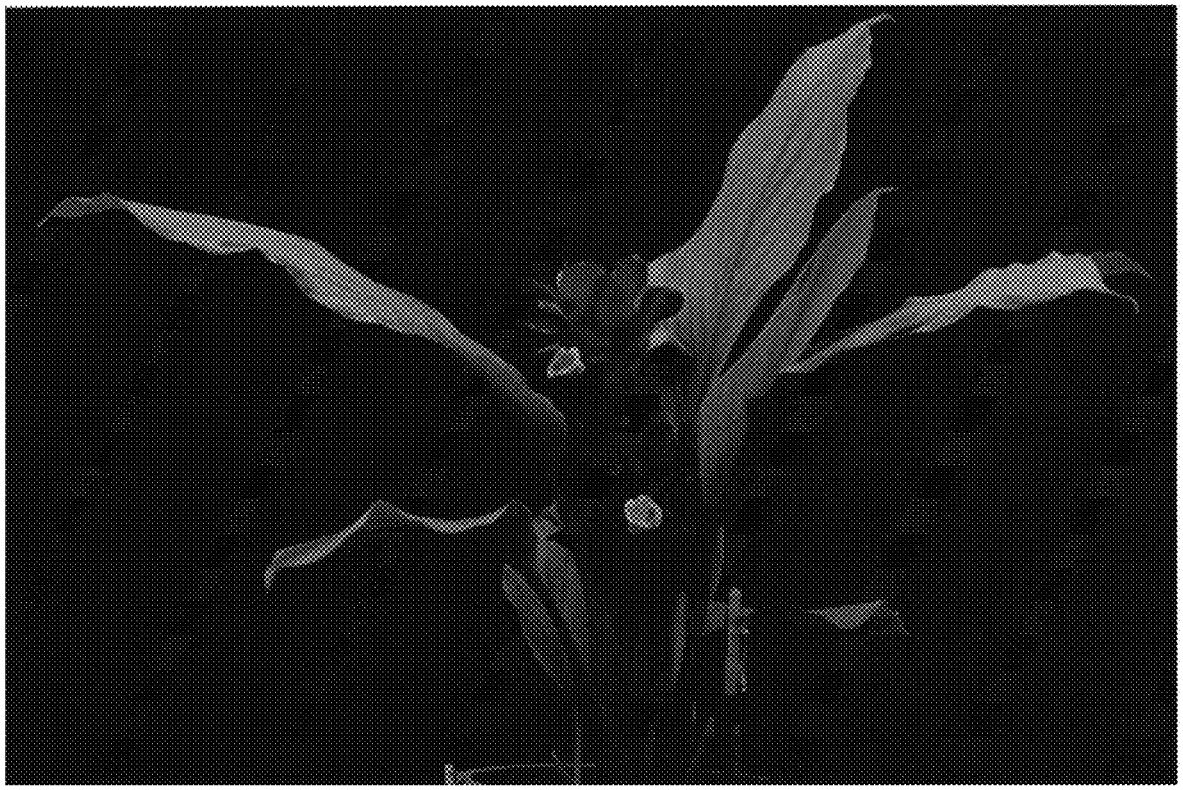

* * * * *